US012300373B2

United States Patent
Chen et al.

(10) Patent No.: US 12,300,373 B2
(45) Date of Patent: *May 13, 2025

(54) PATIENT CARE UNIT ORDER CONFIRMATION

(71) Applicant: CareFusion 303, Inc., San Diego, CA (US)

(72) Inventors: Evan Chen, San Diego, CA (US); Lisa Diggett, Olathe, KS (US); Robert M. Regedanz, San Diego, CA (US); Michael K. Workman, San Diego, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/648,160

(22) Filed: Apr. 26, 2024

(65) Prior Publication Data

US 2024/0274257 A1 Aug. 15, 2024

Related U.S. Application Data

(63) Continuation of application No. 17/321,346, filed on May 14, 2021, now Pat. No. 11,972,851.
(Continued)

(51) Int. Cl.
*G16H 20/13* (2018.01)
*G06F 21/31* (2013.01)
(Continued)

(52) U.S. Cl.
CPC ............. *G16H 20/13* (2018.01); *G06F 21/31* (2013.01); *G16H 10/60* (2018.01); *G16H 20/17* (2018.01)

(58) Field of Classification Search
CPC ........ G16H 20/13; G16H 10/60; G16H 20/17; G16H 40/60; G06F 21/31
See application file for complete search history.

(56) References Cited

U.S. PATENT DOCUMENTS

| 6,985,870 B2 | 1/2006 | Martucci et al. |
| 9,603,995 B2 | 3/2017 | Rosinko et al. |

(Continued)

FOREIGN PATENT DOCUMENTS

| EP | 3421064 A1 | 1/2019 | |
| WO | WO-9910830 A1 | 3/1999 | |
| WO | WO-2015198874 A1 * | 12/2015 | ............. G06F 19/00 |

OTHER PUBLICATIONS

Proceedings of a summit on preventing patient harm and death from i.v. medication errors: Jul. 14-15, 2008. Rockville Maryland. American Journal of Health-System Pharmacy: 65.24: 2367(13). American Society of Health-System Pharmacists. (Dec. 15, 2008)) ( Year: 2008).*

(Continued)

*Primary Examiner* — Linh Giang Le
(74) *Attorney, Agent, or Firm* — Morgan, Lewis & Bockius LLP

(57) ABSTRACT

The disclosed systems and methods provide patient care unit (PCU) order confirmation. A method may include authorizing a user to operate a medication delivery device. The method may also include retrieving, in response to the authorizing, a user history associated with the user, wherein the user history includes one or more dispensing records for pending medications. The method may also include determining, based on a context that includes the user history, one or more medication order candidates for present administration. The method may also include presenting a user interface for confirming a medication order from the one or more medication order candidates. The method may also (Continued)

include configuring at least one parameter of the medication delivery device based on the confirmed medication order received from the user interface.

20 Claims, 5 Drawing Sheets

Related U.S. Application Data

(60) Provisional application No. 63/029,300, filed on May 22, 2020.

(51) Int. Cl.
*G16H 10/60* (2018.01)
*G16H 20/17* (2018.01)

(56) References Cited

U.S. PATENT DOCUMENTS

| | | |
|---|---|---|
| 2006/0031094 A1 | 2/2006 | Cohen et al. |
| 2016/0339167 A1* | 11/2016 | Ledford ................. G16H 70/40 |
| 2017/0372245 A1* | 12/2017 | Gupta ................... G06Q 50/22 |
| 2019/0001057 A1 | 1/2019 | Tsoukalis |

OTHER PUBLICATIONS

International Preliminary Report on Patentability from the International Preliminary Examining Authority for Application No. PCT/US2021/033253, dated Aug. 8, 2022, 19 pages.
International Search Report and Written Opinion for Application No. PCT/US2021/033253, dated Aug. 20, 2021, 14 pages.
Written Opinion of the International Preliminary Examining Authority for Application No. PCT/US2021/033253, dated May 2, 2022, 8 pages.

\* cited by examiner

DISPLAY 342A

PLEASE LOGIN FOR ACCESS

---

DISPLAY 342B

Clinician: Jane Smith          Administration Time: 11:00 AM, 5/1/2020
Patient: John Doe              Location: Room 215
Order: Heparin, via IV, 25000 units / 500 ml, 200 units / hour

1. CONFIRM ORDER          2. SELECT DIFFERENT ORDER

---

DISPLAY 342C

Select an order:
1. John Doe, Heparin, via IV, 25000 units / 500 ml, 200 units / hour, 11:00 am
2. John Doe, Aminophylline, via IV, 2000 mg / 250 ml, 0.5 mg/kg/hr, 11:20 am
3. Robert Grant, D5W, via IV, 0.45NaC1 w/ 20 mEq KC1, 125 ml/hr, 12:00 pm

FIG. 3

PATIENT CARE UNIT ORDER CONFIRMATION

CROSS REFERENCE TO RELATED APPLICATIONS

This application is a continuation of U.S. application Ser. No. 17/321,346, filed on May 14, 2021, now U.S. Pat. No. 11,972,851, which claims the benefit of priority of U.S. Provisional Application No. 63/029,300, filed on May 22, 2020, the entirety of each of which is incorporated herein by reference for all purposes.

TECHNICAL FIELD

The present disclosure generally relates to medical devices, and more specifically relates to methods and systems for order confirmation on medical devices.

BACKGROUND

To treat patients, physicians and other medication personnel may use patient care devices ("PCDs"), also referred to herein as patient care units ("PCUs"), which may include various medical devices such as a single or multi-channel infusion pump, a vital signs monitor, a medicant dispensing device (e.g., cabinet, tote), a medication preparation device, an automated dispensing device, a module coupled with one of the aforementioned (e.g., a syringe pump module configured to attach to an infusion pump), or other similar devices. PCUs may be utilized to apply intravenous ("IV") infusion therapy to treat various medication complications in patients. IV infusion therapy typically involves infusing medication fluids, such as drugs or nutrients, from a fluid supply, such as a bag, bottle or other container, through the tube of a fluid administration set to a cannula inserted into a patient's blood vessel. Other medications may be ordered by a physician for a patient, such as pills or liquids, to be taken by other delivery routes, such as orally by the patient.

In some cases, a physician may order multiple medications for a single patient, and these are to be administered at particular times of a day or over a number of days resulting in a list of "pending medication orders" for the patient. In some implementations, the administration of multiple medications must occur sequentially and in other cases, there is an overlap of the administration of medications. In yet some implementations, the administration of certain medications must occur at a certain time before or after the administration of another medication or medications.

Since a patient may be associated with a treatment regimen that includes multiple pending medication orders with complex administration rules, it becomes increasingly important to reduce the risk of medication errors when programming and configuring PCUs for the patient. Medication errors may include, for example, incorrect medication, incorrect dosage amount, incorrect administration timing, incorrect delivery route, or incorrect order sequence. One approach for reducing medication errors is to provide barcode labels or radio frequency identification (RFID) tags on medications, which are then scanned for automatic entry into a PCU. However, this only ensures that the PCU is correctly programmed according to the medication label or tag, and does not necessarily verify correctness with a patient treatment regimen, which may be managed by an upstream electronic medical record (EMR) management system. In some situations, such as when treating a patient in an emergency room setting, the patient may not yet be registered into the EMR management system, or the EMR management system may be unavailable. In this case, manual entry of medication orders into PCUs may be unavoidable, which may introduce data entry errors. In some cases, the PCU may have information to automatically administer drugs, but the information may be outdated or superseded by subsequent events which may introduce errors in the administration by the PCU.

Accordingly, there is a need for improved systems and methods of order confirmation on medical devices, such as PCUs.

SUMMARY

According to various implementations, the disclosure relates to a medication delivery device comprising: a display; and a processor configured, at least in part, by instructions stored in a memory to: receive a credential associated with a user; authorize the user to operate the medication delivery device, said authorization based at least in part on the credential; retrieve, in response to the authorizing, a user history associated with the user, wherein the user history includes one or more dispensing records for pending medications; receive a patient and order agnostic user input to begin administration of a medication; determine, based on a context that includes the user history, one or more medication order candidates for present administration; present, via the display, a user interface for confirming a medication order from the one or more medication order candidates; and configure at least one parameter of the medication delivery device based on the confirmed medication order received from the user interface.

In some implementations, the processor is configured to retrieve the one or more dispensing records from a most recent set of dispensing records associated with the user. In some implementations, the processor is configured to transmit a request, to a remote database via a network, to retrieve the user history, the request including an identifier of the user. In some implementations, the context includes a location or care area of the medication delivery device, and a dispensing record includes information identifying a dispensing location or dispensing care area, and the processor may be configured to determine the one or more medication order candidates includes the processor configured to identify a medication order candidate based on a correspondence between the location or care area of the medication delivery device and the dispensing location or dispensing care area. In some implementations, the context includes a current time, and a dispensing record includes an administration time for a pending medication, and the processor may be configured to determine the one or more medication order candidates includes the processor configured to identify a medication order candidate based on a correspondence between the current time and the administration time.

In some implementations, the context includes a delivery route for administering the medication with the medication delivery device, and the processor may be configured to filter the one or more medication order candidates based on a correspondence between the delivery route and delivery route information associated with respective medication order candidates. The device may further include a plurality of administration channels; and the processor may be further configured to receive a selection identifying a first channel of the plurality of channels to administer the medication, and the delivery route for the first channel included in the plurality of administration channels is different from another delivery route for a second channel included in the plurality of administration channels.

In some implementations, the processor is configured to receive the credential associated with the user via at least one of: a barcode scanner, a radio frequency identification (RFID) reader, a smart card reader, a near-field communication reader, or a biometric sensor. In some implementations, the medication delivery device comprises an infusion pump, and wherein the at least one parameter of the medication delivery device includes pumping parameter. Other aspects include corresponding methods, apparatuses, and computer program products for implementation of the system.

According to various implementations, the disclosure relates to a method for providing order confirmation at a medication delivery device, the method comprising: receiving a credential associated with a user; authorizing the user to operate a medication delivery device based at least in part on the received credential; retrieving, in response to the authorizing, a user history associated with the user, wherein the user history includes one or more dispensing records for pending medications; receive a patient and order agnostic user input to begin administration of a medication; determining, after receiving the patient and order agnostic user input, based on a context that includes the user history, one or more medication order candidates for present administration; presenting, via display device, a user interface for confirming a medication order from the one or more medication order candidates; and configuring at least one parameter of the medication delivery device based on the confirmed medication order received from the user interface. Other aspects include corresponding systems, apparatuses, and computer program products for implementation of the method.

Further aspects of the subject technology, features, and advantages, as well as the structure and operation of various aspects of the subject technology are described in detail below with reference to accompanying drawings.

DESCRIPTION OF THE FIGURES

Various objects, features, and advantages of the present disclosure can be more fully appreciated with reference to the following detailed description when considered in connection with the following drawings, in which like reference numerals identify like elements. The following drawings are for the purpose of illustration only and are not intended to be limiting of this disclosure, the scope of which is set forth in the claims that follow.

FIG. 3 is a diagram showing example user interfaces displayed on the infusion pump or controller of FIG. 2, according to various aspects of the subject technology.

DESCRIPTION

While aspects of the subject technology are described herein with reference to illustrative examples for particular applications, it should be understood that the subject technology is not limited to those particular applications. Those skilled in the art with access to the teachings provided herein will recognize additional modifications, applications, and aspects within the scope thereof and additional fields in which the subject technology would be of significant utility.

To avoid medication errors and ensure the highest quality of care, healthcare best practices may encourage automated monitoring of the devices and intelligent parameter limits for inputs provided to the devices to ensure the correct administration of medication orders. Since patient care units, or PCUs, are centrally positioned in the healthcare device chain, PCUs may be ideally positioned to provide medication order confirmation prior to administration. After a clinician is authorized to control a PCU, the PCU may retrieve remote data from a healthcare server or database that includes the clinician's user history, such as dispensing records. The dispensing records may include pending records for pending medications. The PCU may assemble a context from the remote data and other local data, and determine, using the context, a next medication order for administration. A user interface may be presented on the PCU to confirm the next medication order. After confirmation, the PCU may be automatically programmed with the correct parameters for administration, such as pumping parameters for an infusion pump.

By enabling the PCU to provide order confirmation, several separate confirmation steps may be consolidated at the PCU, thereby streamlining patient care and avoiding further steps that may introduce mistakes and errors. For example, scanning of individual medications may be avoided and the PCU may be directly programmed and configured based on the next medication order. In addition, scanning of an identifier tag attached to the patient may be avoided by using a patient ID associated with the PCU, or by using geolocation to determine the correct patient for the next administration. All of the data may be consolidated and displayed at the PCU, and the clinician only needs to confirm that everything is correct to continue with administration.

Figure 1:
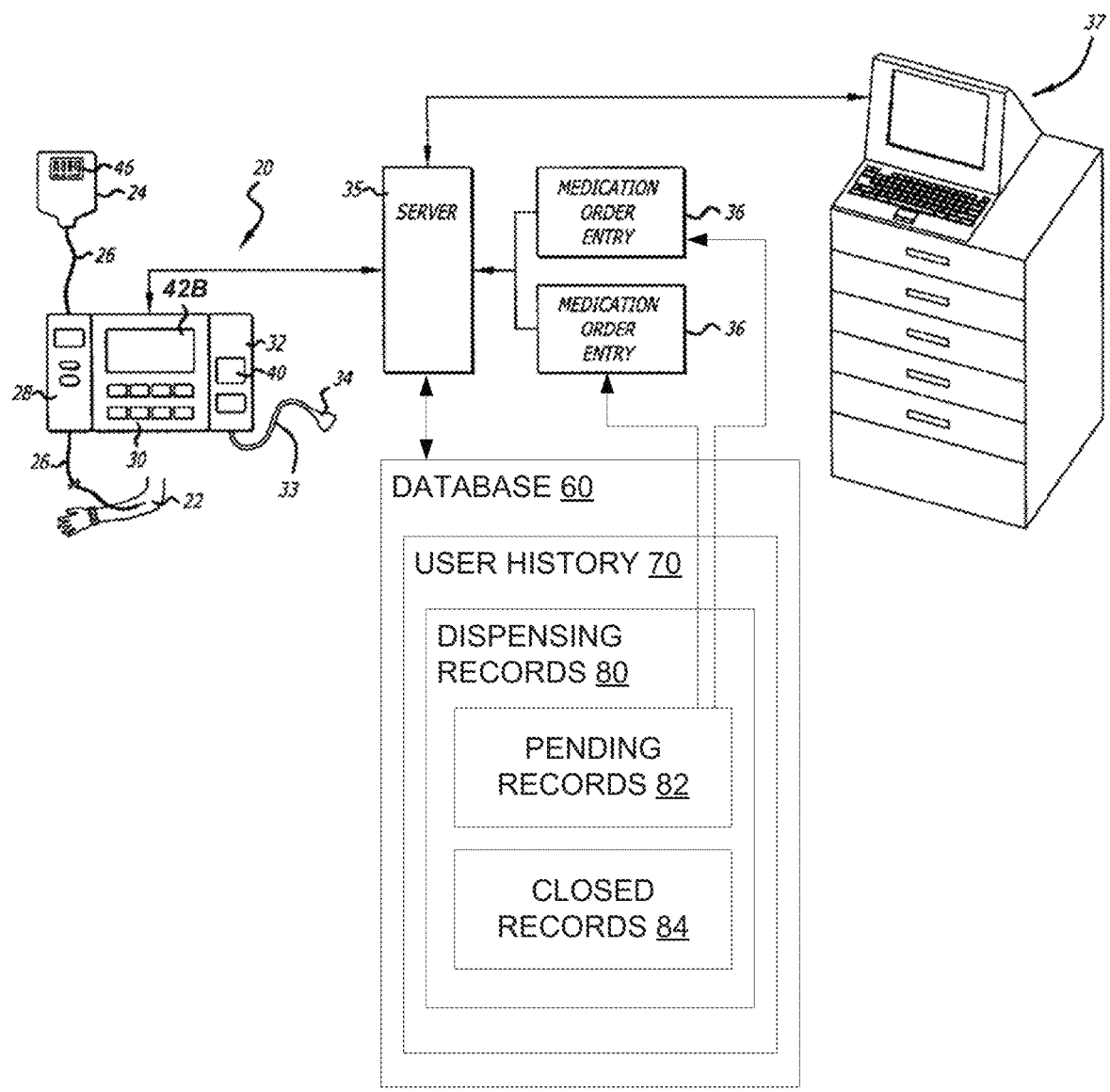
FIG. 1 is a partial block diagram of a system in which a patient care unit (PCU), including an infusion device and associated controller, are connected to a healthcare facility server to confirm a medication order upon identification of the clinician by the infusion pump or controller, and also shows the interaction of an automated dispensing machine with the server, according to various aspects of the subject technology.

Referring now in more detail to the drawings for purposes of illustration of implementations of the invention, wherein like reference numerals designate corresponding or like elements among the several views, there is shown in FIG. 1 a partial block diagram of a system in accordance with certain aspects of the invention. The patient care unit (PCU) in the example shown in FIG. 1 is an infusion pump system 20, which is connected to a patient 22 to infuse medication fluid from an IV fluid container 24, such as a bag, to patient 22 through a fluid administration set 26. The pump system includes an infusion pump 28 located at the left side of a controller 30 and an auto identification module 32 or "auto ID module" located to the right side of the controller. The identification module in this case includes a tethered 33 bar code reader 34.

The controller 30 is connected with a server 35, which may take the form of any server or servers in a health care facility. The box 35 identified as "server" may be a single server or it may comprise multiple servers or computers and memory for data storage. Server 35 may be in communication with database 60, which may store patient identification data as well as pending medication orders for patients admitted to the health care facility. It may also store clinician identification data and other data, such as user history 70 associated with a particular user or clinician. User history 70 may include dispensing records 80, which may include a record for each medication dispensed by the association clinician. For example, when the clinician uses automated dispensing machine ("ADM") 37 to retrieve a medication, an associated record may be created in pending records 82. Pending records 82 may be associated with open or pending medication orders, whereas closed records 84 may be associated with medication orders that have already been administered. While pending records 82 and closed records 84 are shown as separate record sets, it should be understood that both record sets may be stored in a single table with record fields that identify which records are pending or closed.

The "server" identified by numeral 35 may also include, for purposes of convenience of discussion and illustration, a server of the company that provides the infusion pump system 20 and establishes communication protocols between that infusion pump system and health care facility servers. The server 35 electronically receives medication order entries 36 from one or more sources, such as the pharmacy information system (PIS), laptop computers, physician order entry devices, personal digital assistants ("PDA"), and other devices. Medication order entries 36 may also be entered into the server by the pharmacy. Dispensing records 80 may each be associated with a corresponding medication order entry 36. The controller 30 may be in communication with the server 35 by any wired or wireless means and the server may be in communication with other devices by wired or wireless means.

An automated dispensing machine ("ADM") 37 is also shown and typically includes medications for the patients in the vicinity. The ADM has a processor, termed a dispensing processor 50 (shown in FIG. 5), and may require clinician identification before permitting any medications to be withdrawn. The dispensing processor may permit only certain clinicians to remove certain items from the ADM. The ADM may also contain "controlled items" which, for the purposes herein, may be any item desired to be tracked by the healthcare facility in which the ADM is located. This may include narcotics but also may include items of much less sensitivity.

Figure 2:
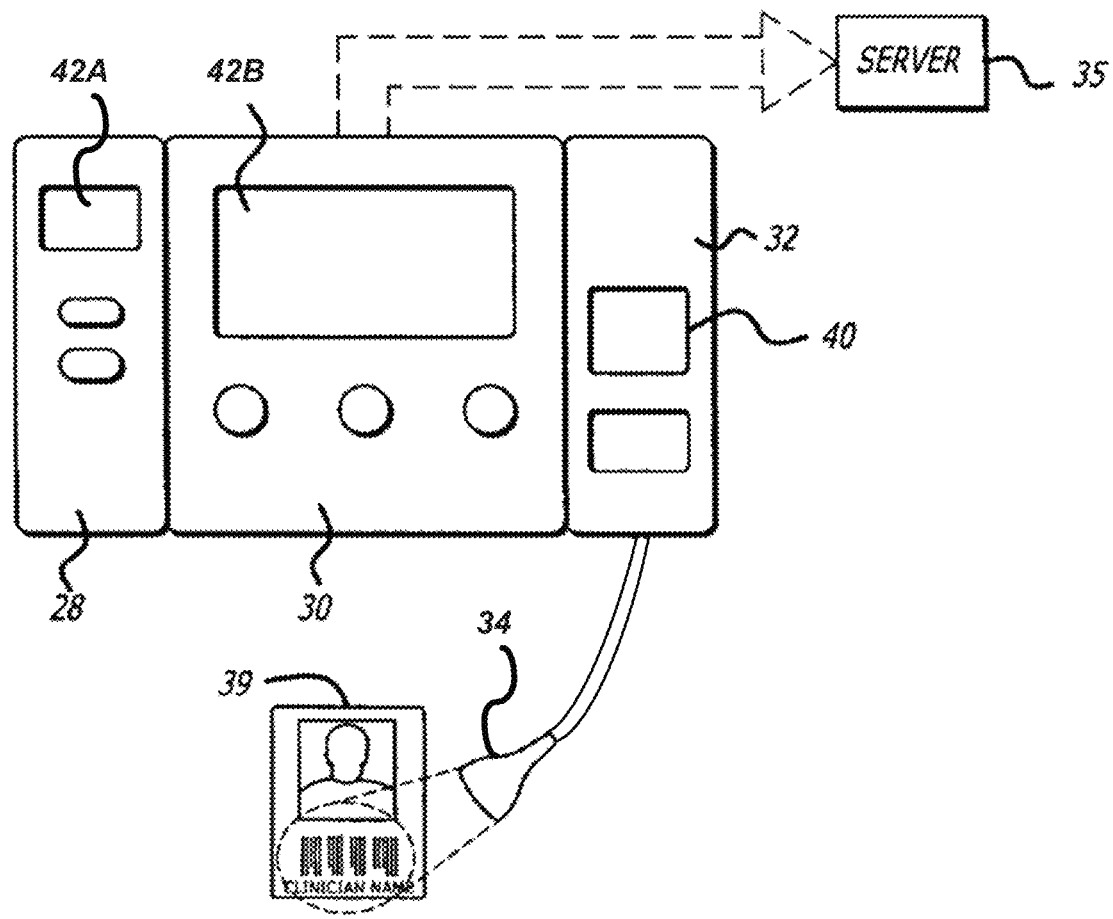
FIG. 2 is a diagram showing a means of authorizing a clinician through the use of an auto identification module connected to a controller associated with the infusion pump of FIG. 1, according to various aspects of the subject technology.

FIG. 2 is a diagram showing a means of authorizing a clinician through the use of an auto identification module connected to a controller associated with the infusion pump of FIG. 1, according to various aspects of the subject technology. Upon initial power up of the controller 30, the controller 30 may prompt the clinician to login. The clinician may have an identification 39 that can be scanned by an embedded code reader 40 or a tethered 33 code scanner 34. As shown in FIG. 2, the reader 40 and the scanner 34 form parts of an automated identification module 32 that can be attached to a PCU. The code reader 40 and/or code scanner 34 may include a radio frequency identification (RFID) reading element(s), smart card reading element(s), near-field communication reading element(s), or biometric sensing element(s) to process (e.g., collect, verify, authenticate) credentials provided by the clinician. The automated identification module 32 may communicate by wired or wireless means with the controller 30. In one case, the controller 30 includes a communications interface ("CI Board") containing a processor, programming, and a substantial memory. The CI Board is in contact with the automated identification module 32. Upon receiving a clinician credential, the CI Board may send a message to the controller 30 indicating that a clinician is requesting to login. The message may include the clinician credential received. In some implementations, the automated identification module 32 may validate and/or verify the credential and include a result of the validation or verification in the message provided to the controller 30. In some implementations, the functions of the CI Board are all performed by a processor of controller 30 and/or by other components within controller 30. A processor of controller 30 may then verify whether the clinician is authorized to control infusion pump system 20. For example, in some implementations, infusion pump system 20 may be assigned to a specific patient identifier, and a lookup may be performed to verify whether the clinician is authorized to provide care for a patient associated with the specific patient identifier.

Upon a successful authorization of the clinician's credentials, display 42A of infusion pump 28 and/or display 42B of controller 30 may show a user interface for confirming a next medication order. As discussed below in conjunction with FIG. 3, the next medication order may be intelligently selected based on a context, which includes the user history 70 associated with the clinician. The user interface may show the next medication order pre-selected on the user interface and ask for confirmation prior to programming and configuring infusion pump 28.

As used herein, the term "medication" is meant to be understood in a broad sense as pertaining to medical care. "Medication" would include oral medications and infusions of medications, but is also meant to include physical therapy, taking vital signs, preparation for surgery, and other medical care. Also, "administer" is meant to be understood in a broad sense as providing medical care. "Administer" is meant to cover the dispensing of medications, such as oral medications, as well as performing infusions on a patient and other provisions of medical care. The illustrative controller 30 discussed herein and shown in the drawings as a separate unit may actually be a part of an infusion pump or other medical instrument. The order of identifying individuals or medications or performing steps is provided as implementations. The identifications may be performed in different orders in certain healthcare facilities, the orders presented here are implementations.

FIG. 3 is a diagram showing example user interfaces displayed on the infusion pump or controller of FIG. 2, according to various aspects of the subject technology. With respect to FIG. 3, display 342A, display 342B, and display 342C may correspond to display 42A or display 42B from FIGS. 1 and 2. In some implementations, display 342A-342C may be shown on a remote device, such as a tablet, smartphone, laptop, or desktop computer.

Display 342A may be shown after startup of controller 30. As shown in display 342A, the user interface displays no information regarding any patients or orders and waits for a clinician to successfully login before displaying any information. Assuming that the clinician is successfully authenticated using the procedures described above, the user interface may transition to display 342B.

As shown in display 342B, a next medication order for administration is already preselected and shown to the clinician, with various details of the medication order indicated including the associated clinician, the associated patient, the administration time, the location, and the medication order including information such as medication name, administration route, drug concentration, and pumping parameters such as volume to be infused ("VTBI") and infusion rate over time. If everything appears correct, the clinician may simply indicate the "confirm order" option, and the infusion pump 28 may be programmed according to the pumping parameters in the indicated order. Example steps for preselection of a medication order are described in further detail below in conjunction with FIG. 4.

If the preselected next medication order is not the desired order, the user interface may include a control element to receive an input to select a different order. In FIG. 3B, the user interface includes a "select different order" control element to receive this input. Once activated, the control element may cause a transition of the user interface to present display 342C. In display 342C, a list of candidate orders are shown. The orders may be associated with a selection control element that can be interacted with to receive a selection for a desired medication order. The list of candidate orders may be narrowed based on contextual information detected or accessible by the system. Example steps for narrowing orders are described in further detail below in conjunction with FIG. 4.

Figure 4:
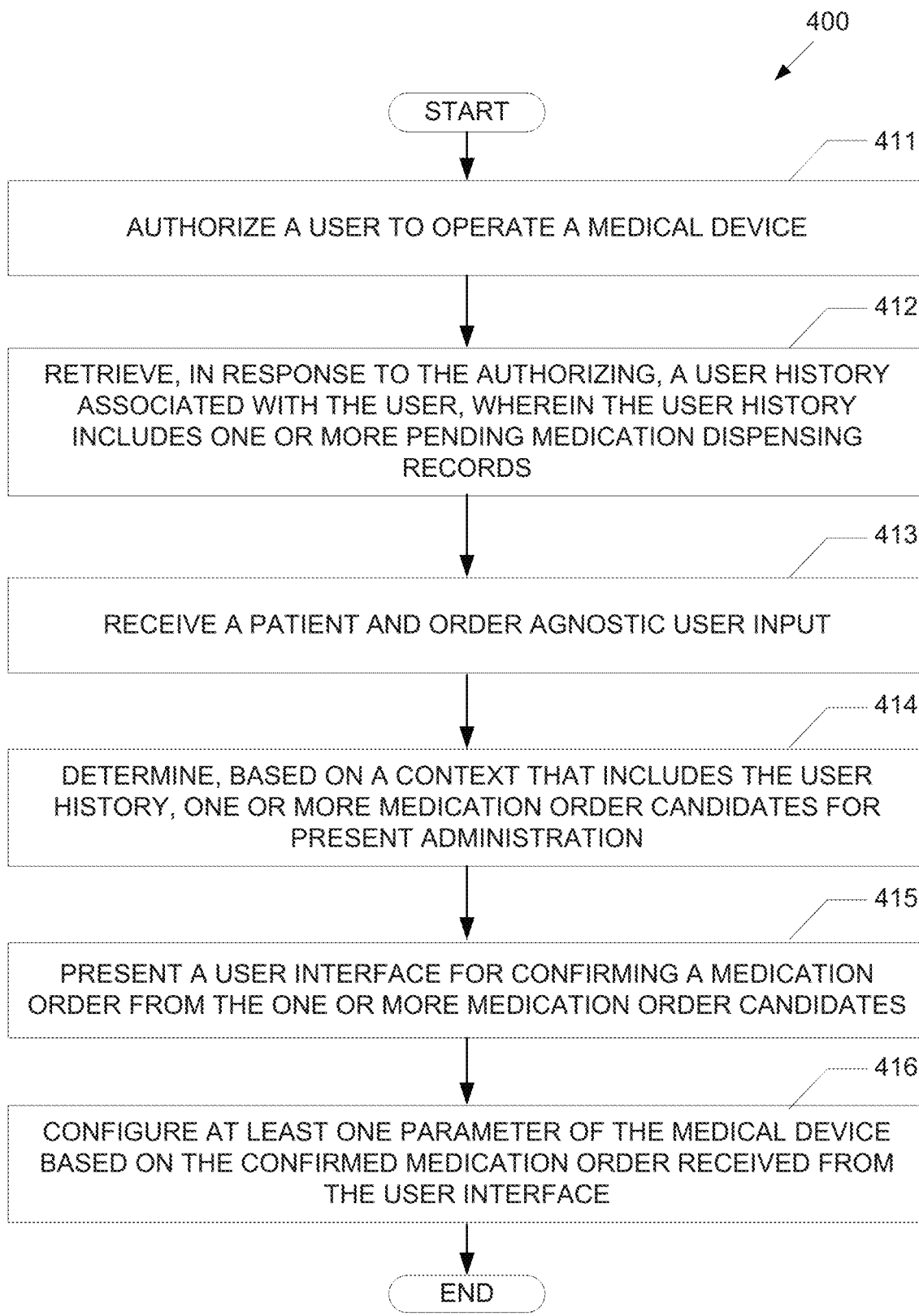
FIG. 4 depicts an example process for providing patient care unit (PCU) order confirmation on a medical device, according to various aspects of the subject technology.

FIG. 4 depicts an example process 400 for providing patient care unit (PCU) order confirmation on a medical device, according to various aspects of the subject technology. For explanatory purposes, the various blocks of example process 400 are described herein with reference to FIGS. 1A-3, and the components and/or processes described herein. The one or more of the blocks of process 400 may be implemented, for example, by one or more of computing devices described here, such as a PCU, module coupled with a PCU, or a server of the healthcare facility (e.g., server 35). In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example flow diagram, a medical device or PCU, such as infusion pump system 20, may authorize a user, such as a clinician, to operate the infusion pump system 20 (411). As described above, the user may use a badge with a barcode, RFID tag, or other identifier as a credential for authorization. Infusion pump system 20 may use a corresponding reader, such as tethered 33 code reader 34, to receive the credential. By communicating with server 35 and/or database 60, infusion pump system 20 may verify that the credential is authorized.

Process 400 may continue with retrieving, in response to the authorizing, a user history associated with the user, wherein the user history includes one or more pending medication dispensing records (412). Referring to FIG. 1, this may correspond to infusion pump system 20 querying database 60 to retrieve a user history 70 associated with the user, wherein the user history 70 includes dispensing records 80 with pending records 82. For example, the user history 70 may be associated with a user ID that matches the previously authorized clinician ID. In another example, user history 70 may be associated with another user ID, e.g. a supervisor, that is authorized according to access privileges granted by the authorized clinician ID. As shown in FIG. 1, each of pending records 82 may be created when the associated user retrieves medication from a dispensing device, such as ADM 37, and each record may reference an associated medication order entry 36, which may be provided by a pharmacy, as described above. In some cases, pending records 82 may include a large number of records. In this case, rather than retrieving all of pending records 82, only a most recent set of dispensing records may be retrieved, e.g. up to a fixed number or according to a time cutoff. The time cutoff may be dynamically assessed based on information associated with the authorized user. For example, a time and attendance system may include a shift start time for the authorized user. The shift start time may represent the earliest moment in the current day that could be associated with a dispense event related to the authorized user.

According to various implementations, process (in some implementations, optionally) receives a patient and order agnostic user input to begin administration of a medication (413). For the purposes of this disclosure, a "patient and order agnostic user input" means an input that does not include any information identifying a patient or an order. In this regard, the system may receive information about a medication being administered but does not know to what patient that medication is being administered or whether the medication is currently associated with an order.

Process 400 may continue with determining, based on the patient and order user input (if available) and a context that includes the user history, one or more medication order candidates for present administration (414). When receiving patient and order agnostic user input, the system does not currently know to what patient to which the medication delivery device is designated for or associated with, and has not currently associated an order with the patient or a medication being programmed in the device. Accordingly, the system performs an order correlation independent and before the patient or medication is identified to the system. Instead, the pending records 82 in the retrieved user history 70, and various other factors may be considered for determining the medication order candidates. The factors in the context can be used to narrow the medication order candidates to a list of most likely next medication orders, for example by assigning a relevance weighting to each medication order candidate, wherein each of the factors in the context may contribute a weighted value for each medication order candidate. After the weighting, the list of medication order candidates can be narrowed or pruned using one or more factors, such as falling below a weighting threshold, or meeting a maximum number of candidates (e.g. by including 3 candidates with the highest weight values).

In some implementations, the context may include a location and/or defined care area of the medical device. For example, infusion pump system 20 may be preprogrammed with a deployment location and/or care area, or otherwise include location tracking components, such as global positioning system (GPS) sensors or radio triangulation sensors to determine a current location.

In some implementations, the context includes a location or care area of the medication delivery device. For example, a dispensing record may include information identifying a dispensing location or dispensing care area. In this regard, the system may determine one or more medication order candidates by identifying a medication order candidate based on a correspondence between the location or care area of the medication delivery device and the dispensing location or dispensing care area. Such correspondence may include, but is not limited to, a difference or meeting one or more thresholds (e.g. number of matching characteristics), or may be configurable. Correspondence may also be dynamic based on medication, patient, care area, and the like.

By querying server 35 for patient data at the current location, the possible patients can be limited to those located at the current location of the medical device, near the current location of the medical device, or within a defined care area of the medical device. Accordingly, the medication order candidates can be narrowed to orders specifically for the patients within the location or defined care area of the medical device.

In some implementations, the context may include a current time and an administration time of the medication order. For example, medication orders with an administration time that are closer to the current time may be favored for selection as medication order candidates. The context may also include a dispensing time of the medication order, which may be compared to the current time. For example, a most recently dispensed medication order may be favored for selection, since the latest dispensed item may be the most urgent for the clinician. A least recently dispensed medication order may also be favored for selection, since the oldest dispensed item may be the first to dispense in a sequence of medications. If rules are defined for ordered administration of multiple medication orders, then these rules may also be factored when selecting and weighting medication orders.

In some implementations, the context may include a patient associated with the medical device. For example, if the medical device is configured to care only for a specific patient, then the medication order candidates can be limited to that specific patient.

In some implementations, the context may include a delivery route for the medication orders. For example, infusion pump system 20 may only accept medication orders intended for IV delivery, rather than other routes such as oral administration.

In some implementations, the context may exclude a positive identification of the patient, for example when the patient is newly admitted into an emergency room setting and no EMRs exist yet for the patient. In this case, the medication order candidates can still be determined based on the other context factors described above. In a similar fashion, when other factors are missing or unavailable, then the other remaining factors in the context may still be used to determine the medication order candidates.

According to some implementations, context includes a delivery route for administering the medication with the medication delivery device, and the system may filter the one or more medication order candidates based on a correspondence between the delivery route and delivery route information associated with respective medication order candidates. As described previously, correspondence may include, but is not limited to, a difference or meeting one or more thresholds (e.g. number of matching characteristics), or may be configurable. Additionally, in some implementations, the medication delivery device may include a plurality of administration channels. In this regard, the system may be configured to receive a selection identifying a first channel of the plurality of channels to administer the medication, and the delivery route for the first channel included in the plurality of administration channels may be different from another delivery route for a second channel included in the plurality of administration channels.

Process 400 may continue with presenting a user interface for confirming a medication order from the one or more medication order candidates (415). For example, after narrowing the medication order candidates, if only a single medication order candidate remains, then that order may be selected for confirmation. However, if multiple medication order candidates remain, the most likely next order may be preselected, as shown in the user interface of display 342B of FIG. 3, wherein the other medication order candidates can still be selected using the selection user interface shown in display 342C. The most likely next order may be selected by, for example, selecting the candidate with the highest weighting.

For example, the selection list in display 342C may be sorted in order of weighting, wherein order #1 is determined to be the most likely next medication order and order #3 is determined to be the least likely next medication order. For example, John Doe may be located at room 215, whereas Robert Grant may be located at room 216. Since the medical device is in room 215, the medication orders for John Doe are listed first. Additionally, the current time may be 11:00 AM, which indicates that the administration of Heparin is now due, whereas the administration of Aminophylline is still 20 minutes in the future. Thus, the order that has the closest administration time is preferred and listed as order #1.

According to some implementations, the user may perform a dispense event, and thus be associated with the dispense event by the system. The user then associates with the pump via a credential. Order information from the dispense may be provided and confirmed at the pump before the user enters any order specific information.

Process 400 may continue with configuring at least one parameter of the medical device based on the confirmed medication order received from the user interface (416). Thus, after the clinician confirms the pre-selected order in display 342B or selects a different order in display 342C, the pumping parameters of the confirmed order may be programmed into infusion pump 28, including e.g. VTBI and infusion rate. Once the administration is completed, then the medical device may send a notification to server 35 to cause the associated record in pending records 82 to be moved to closed records 84.

Many aspects of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
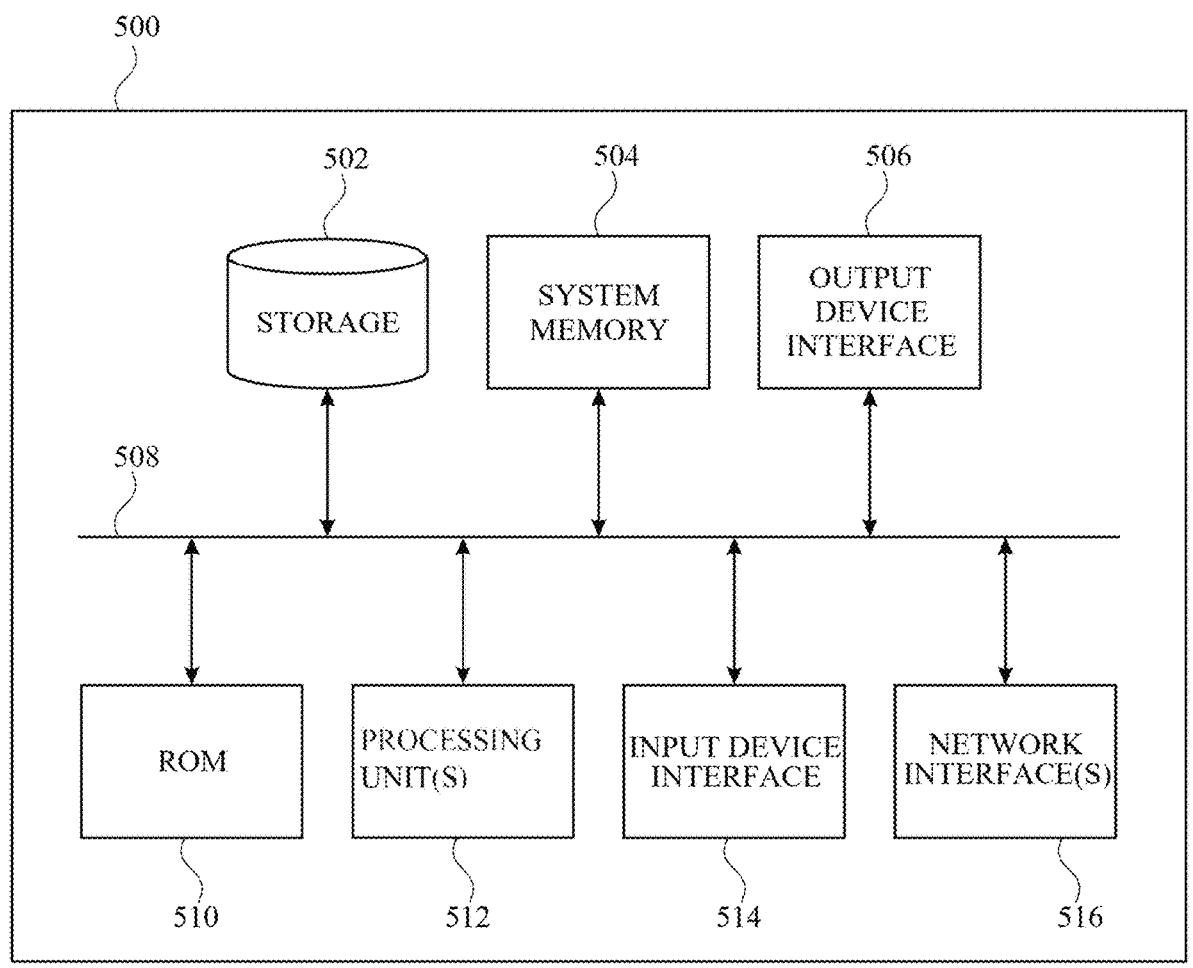
FIG. 5 is a conceptual diagram illustrating an example electronic system for providing patient care unit (PCU) order confirmation, according to various aspects of the subject technology.

FIG. 5 is a conceptual diagram illustrating an example electronic system 500 for providing patient care unit (PCU) order confirmation, according to various aspects of the subject technology. Electronic system 500 may be a computing device for execution of software associated with one or more portions or steps of process 400, or components and processes provided by FIGS. 1-4. Electronic system 500 may be representative, in combination with the disclosure regarding FIGS. 1-4, of the infusion pump system 20, the infusion pump 28, or the controller 30 described above. In this regard, electronic system 500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and processes previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Some implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such a random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process in order to execute the processes of some implementations.

Bus 508 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism.

The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As used herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any implementation, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A system, comprising:
   one or more processors;
   a memory device comprising instructions stored thereon that, when executed by the one or more processors, cause the one or more processors to perform operations comprising:
   receiving a user identification for a user;
   automatically retrieving, from one or more databases based on the user identification, a user history associated with the user, the user history referencing one or more medication orders;
   receiving a patient and order agnostic user input to begin administration of a medication;
   determining, based on a context that includes the user history, and before any patient or order is identified as being associated with the user input, one or more medication order candidates for the administration of the medication;
   providing, for display on a display screen, a user interface comprising a list of the one or more medication order candidates for selection responsive to the user input;
   receiving a user selection of a medication order from the one or more medication order candidates displayed in the user interface; and
   automatically programming, based on and after the user selection, a medical device with at least one parameter according to the selected medication order.

2. The system of claim 1, wherein retrieving the user history comprises retrieving, based on the user identification, dispensing records for medications dispensed from one or more medication dispensing machines, each dispensing record referencing a respective medication order.

3. The system of claim 2, wherein the dispensing records are retrieved for a period of time starting at a shift start time of the user and the dispensing records are for medications dispensed by the user from one or more medication dispensing machines.

4. The system of claim 2, the operations further comprising:
   determining the one or more medication orders, from a plurality of medication orders, based on the one or more medication orders being dispensed at a time closest to a current time.

5. The system of claim 2, the operations further comprising:
   determining the one or more medication orders, from a plurality of medication orders, based on the one or more medication orders being due for administration to a patient at a time closest to a current time.

6. The system of claim 2, wherein the medical device comprises an infusion device separate from the one or more medication dispensing machines, wherein the at least one parameter of the medical device comprises a pumping parameter, and wherein
   determining the one or more medication orders, from a plurality of medication orders, based on the one or more medication orders being identified as intended for intravenous (IV) delivery.

7. The system of claim 6, the operations further comprising:
   receiving an indication that the infusion device completed an administration of the medication order; and
   responsive to receiving the indication, closing a pending record associated with a dispense event for the medication order.

8. The system of claim 1, the operations further comprising:
   identifying a location or care area associated with the medical device or the user, and
   determining the one or more medication order candidates only for patients currently associated with the identified location or care area.

9. The system of claim 1, the operations further comprising:
   identifying a patient associated with the medical device based on the selected medication order.

10. The system of claim 1, wherein the operations further comprise:
    receiving an indication that the user is authorized to operate the medical device before programming the medical device.

11. A machine-implemented method for determining a medication order for a medical device, the method comprising:
    receiving a user identification for a user;
    automatically retrieving, from one or more databases based on the user identification, a user history associated with the user, the user history referencing one or more medication orders;
    receiving a patient and order agnostic user input to begin administration of a medication;
    determining, based on a context that includes the user history, and before any patient or order is identified as being associated with the user input, one or more medication order candidates for the administration of the medication;
    providing, for display on a display screen, a user interface comprising a list of the one or more medication order candidates for selection responsive to the user input;
    receiving a user selection of a medication order from the one or more medication order candidates displayed in the user interface; and
    automatically programming, based on and after the user selection, a medical device with at least one parameter according to the selected medication order.

12. The machine-implemented method of claim 11, wherein
    retrieving the user history comprises retrieving, based on the user identification, dispensing records for medications dispensed from one or more medication dispensing machines, each dispensing record referencing a respective medication order.

13. The machine-implemented method of claim 12, wherein the dispensing records are retrieved for a period of time starting at a shift start time of the user and the dispensing records are for medications dispensed by the user from one or more medication dispensing machines.

14. The machine-implemented method of claim 12, further comprising:
    determining the one or more medication orders, from a plurality of medication orders, based on the one or more medication orders being dispensed at a time closest to a current time.

15. The machine-implemented method of claim 12, further comprising:
    determining the one or more medication orders, from a plurality of medication orders, based on the one or more medication orders being due for administration to a patient at a time closest to a current time.

16. The machine-implemented method of claim 12, wherein the medical device comprises an infusion device separate from the one or more medication dispensing machines, and wherein the at least one parameter of the medical device comprises a pumping parameter, the method further comprising:
  determining the one or more medication orders, from a plurality of medication orders, based on the one or more medication orders being identified as intended for intravenous (IV) delivery.

17. The machine-implemented method of claim 16, further comprising:
  receiving an indication that the infusion device completed an administration of the medication order; and
  responsive to receiving the indication, closing a pending record associated with a dispense event for the medication order.

18. The machine-implemented method of claim 11, further comprising:
  identifying a location or care area associated with the medical device or the user, and
  determining the one or more medication order candidates only for patients currently associated with the identified location or care area.

19. A non-transitory storage medium comprising instructions that, when read by one or more processors, cause the one or more processors to perform a method comprising:
  receiving a user identification for a user;
  automatically retrieving, from one or more databases based on the user identification, a user history associated with the user, the user history referencing one or more medication orders;
  receiving a patient and order agnostic user input to begin administration of a medication;
  determining, based on a context that includes the user history, and before any patient or order is identified as being associated with the user input, one or more medication order candidates for the administration of the medication;
  providing, for display on a display screen, a user interface comprising a list of the one or more medication order candidates for selection responsive to the user input;
  receiving a user selection of a medication order from the one or more medication order candidates displayed in the user interface; and
  automatically programming, based on and after the user selection, a medical device with at least one parameter according to the selected medication order.

20. The non-transitory storage medium of claim 19, wherein retrieving the user history comprises retrieving, based on the user identification, dispensing records for medications dispensed from one or more medication dispensing machines, each dispensing record referencing a respective medication order, wherein the medical device comprises an infusion device separate from the one or more medication dispensing machines, and wherein the at least one parameter of the medical device comprises a pumping parameter, the method further comprising:
  determining the one or more medication orders, from a plurality of medication orders, based on the one or more medication orders being identified as intended for intravenous (IV) delivery.

* * * * *